United States Patent [19]
Thukral

[11] Patent Number: 6,103,472
[45] Date of Patent: Aug. 15, 2000

[54] METHODS AND COMPOSITIONS FOR IDENTIFYING NOVEL SECRETED MAMMALIAN POLYPEPTIDES IN YEAST

[75] Inventor: Sushil K. Thukral, Thousand Oaks, Calif.

[73] Assignee: Amgen Inc., Thousand Oaks, Calif.

[21] Appl. No.: 09/026,959

[22] Filed: Feb. 20, 1998

[51] Int. Cl.[7] .............................. C12Q 1/68; C12P 19/34
[52] U.S. Cl. ................................................ 435/6; 435/91.2
[58] Field of Search ................................. 435/5, 6, 69.1, 435/91.2, 23.1

[56] References Cited

U.S. PATENT DOCUMENTS

| | | | |
|---|---|---|---|
| 5,037,760 | 8/1991 | Smith et al. | 435/320.1 |
| 5,525,486 | 6/1996 | Honjo et al. | 435/69.1 |
| 5,536,637 | 7/1996 | Jacobs | 435/6 |

FOREIGN PATENT DOCUMENTS

| | | |
|---|---|---|
| 96/40904 | 8/1996 | WIPO . |
| 97/23614 | 7/1997 | WIPO . |

OTHER PUBLICATIONS

Berger And Kimmel, Methods in Enzymology: Guide to Molecular Cloning Techniques, vol. 152, Academic Press, Inc., San Diego, Ca, (1987).

Engels Et Al. Angew. Chem. Intl. Ed., 28 :716–734 (1989).

Imai et al. J. Biol. Chem. 271, 21514–21521 (1996).

Klein et al. Proc. Natl. Acad. Sci. USA 93, 7108–7113 (1996).

Laloux et al. FEBS Letters 289, 64–68 (1991).

Sambrook et al., Molecular Cloning: A Laboratory Manual, Cold Spring Harbor Laboratory Press, Cold Spring Harbor, NY, (1989).

Shirozu et al. Genomics 37, 273–280 (1996).

Steyn et al. Curr. Genetics 28, 526–523 (1995).

Summer–Smith et al. Gene 36 333–340 (1985).

Tashiro et al. Science 261, 600–603 (1993).

Wells et al. Gene, 34:315 (1985).

*Primary Examiner*—Eggerton A. Campbell
*Attorney, Agent, or Firm*—Robert B. Winter; Steven M. Odre; Ron K. Levy

[57] ABSTRACT

Method for identifying novel secreted mammalian proteins in yeast are described. Reporter polypeptides which allow detection of signal sequences by growth selection are also described.

2 Claims, No Drawings

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

AGTCCTCGAG CAACAATGTT GCTGATCAAC T      31

(2) INFORMATION FOR SEQ ID NO:2:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

AGTCGAGCTC TCTACATGGA GATTC      25

(2) INFORMATION FOR SEQ ID NO:3:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

AGTCGCGGCC GCGGATTGCA CTACAGTTAC GGT                                    33

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

AGTCGCGGCC GCAGCGATAC ATCTGTGACA TAC                                    33

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AGCTGTCGAC ATGGGGGTGC ACGAATGTCC T                                      31

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGCTGCGGCC GCCAGGACTG GGAGGCCCAG A                                      31

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

AGCTGCGGCC GCGTGTTCAG CACAGCCCGT CG                                     32

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
AGCTGCGGCC GCGCCCTGCC AGACTTCTAC GG                                          32
```

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
AGCTGCGGCC GCGACGGCTT TATCCACATG CAG                                         33
```

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
AGCTGCGGCC GCTGTTCGGA GTGGAGCAGC TG                                          32
```

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
AGCTGCGGCC GCTCTGTCCC CTGTCCTGCA GG                                          32
```

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
AGTCGTCGAC ATGAAGCTCT GCGTGACTG                                              29
```

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
AGTCGCGGCC GCGTTCAGTT CCAGGTCATA C                                           31
```

(2) INFORMATION FOR SEQ ID NO:14:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:14:

AGTCGTCGAC ATGAAAGTCT CTGCCGCCC                                              29

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

AGTCGCGGCC GCAGTCTTCG GAGTTTGGGT TTG                                         33

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

AGTCGTCGAC ATGAAGGTCT TGGCGGCA                                               28

(2) INFORMATION FOR SEQ ID NO:17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

AGTCGCGGCC GCACATAGCT TGTCCAGGTT G                                           31

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AGTCGTCGAC ATGCACAGCT CAGCACTG                                               28

(2) INFORMATION FOR SEQ ID NO:19:

(i) SEQUENCE CHARACTERISTICS:
        (A) LENGTH: 30 base pairs
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:19:

AGTCGCGGCC GCGTTCTCAG CTTGGGGCAT                                      30

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

AGTCGTCGAC ATGAACTCCT TCTCCACAAG                                      30

(2) INFORMATION FOR SEQ ID NO:21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

AGTCGCGGCC GCGAATCCAG ATTGGAAGCA TC                                   32

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GGAAGGAAAA AAGCGGCCGC AACANNNNNN NNN                                  33

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CGTCATTGTT CTCGTTCC                                                   18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA
```

```
           (xi) SEQUENCE DESCRIPTION: SEQ ID NO:24:

ACTAGCTCCA GTGATCTC                                                          18

(2) INFORMATION FOR SEQ ID NO:25:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:25:

GCTATACCAA GCATACAATC                                                        20

(2) INFORMATION FOR SEQ ID NO:26:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:26:

CTAGCTGGAC ATGGTTCG                                                          18
```

METHODS AND COMPOSITIONS FOR IDENTIFYING NOVEL SECRETED MAMMALIAN POLYPEPTIDES IN YEAST

FIELD OF THE INVENTION

The invention relates to methods for identifying novel secreted mammalian proteins.

BACKGROUND OF THE INVENTION

Proteins destined for transport into or across cell membranes are usually translated with a signal sequence that directs the newly synthesized protein to the appropriate membrane translocation system. The primary structure of signal sequences is highly variable among different proteins. Signal sequences that target proteins for export from the cytosol generally contain a short stretch (7–20 residues) of hydrophobic amino acids. In most cases, the signal sequence is located at the amino terminus of a nascent protein and is proteolytically removed on the trans side of the membrane (e.g. lumen of endoplasmic reticulum, bacterial periplasm, intercisternal space of mitochondria and chloroplasts), although examples of mature proteins containing uncleaved or internal signal sequences have been described. Export signal sequences may be interchanged among different proteins, even proteins of different species of organisms.

Many secreted proteins interact with target cells to bring about physiological responses such as growth, differentiation and/or activation. These activities make secreted proteins biologically interesting molecules which are potentially valuable as therapeutics or as targets for ligands. Of the estimated 60,000 to 100,000 human genes, about 25% carry a signal peptide and about 4% are secreted extracellularly. Clearly, approaches to rapidly and accurately identifying secreted proteins are important components of gene-based drug discovery programs.

With advances in techniques for sequencing cDNAs, many expressed sequence tags (ESTs) have been generated which have enhanced the process of identifying novel secreted proteins as compared to the conventional reverse genetics approaches. However, EST's are small random cDNA sequences and thus it becomes hard to identify secretion signal sequence that is normally present in the 5' end of cDNA encoding secreted protein. Moreover, after an EST carrying a potential secretion signal sequence is identified based on the homology search, it has to be authenticated in a functional assay. Thus a screen based on selection of functional secretion signals from random cDNA libraries would greatly simplify the process of obtaining novel secreted genes.

Secretion signal trap is one such method to clone 5' ends of cDNAs encoding for secreted proteins from a random cDNA library. Generally, signal trapping relies on secretion of a reporter polypeptide by signal sequences present in a cDNA library. The secreted reporter polypeptide may then be detected by a variety of assays based upon, for example, growth selection, enzymatic activity or immune reactivity. Examples of signal trap cloning procedures include the following.

U.S. Pat. No. 5,536,637 and Klein et al. *Proc. Natl. Acad. Sci. USA* 93, 7108–7113 (1996) describe signal trap cloning in yeast using the yeast invertase polypeptide as a reporter.

Imai et al. *J. Biol. Chem.* 271, 21514–21521 (1996) describe signal trap cloning in mammalian cells using CD4 as a reporter and identifying signal sequences by screening for surface expression of CD4 antigen.

U.S. Pat. No. 5,525,486, Shirozu et al. *Genomics* 37, 273–280 (1996) and Tashiro et al. *Science* 261, 600–603 (1993) describe signal trap cloning in mammalian cells and identify signal sequences by screening for surface expression of IL-2 receptor fusion proteins.

U.S. Pat. No. 5,037,760 describes signal trap cloning in Bacillus using α-amylase and β-lactamase as reporter genes.

Published PCT Application No. WO96/40904 describes signal trap cloning by selection for growth of factor-dependent cell lines and screening with tagging reagents for surface expression of growth factor receptors.

Signal sequence trapping using mammalian cells has disadvantages, including low transfection efficiency and difficult recovery of a desired clone from cells that have been transfected with multiple plasmids. Procaryotic cells have a secretion pathway which is not suitable for identifying mammalian secretion signals. By contrast, yeast has the advantages of a short doubling time, high transformation efficiency, and choice of single and high copy plasmid system. Also, yeast has a secretory machinery similar to mammalian cells. Thus, there is a need to develop alternative approaches for rapid and accurate identification of novel secreted mammalian proteins using yeast host cells.

Accordingly, it is an object of the invention to provide signal trap vectors and related methods and compositions for identifying signal sequences in yeast host cells.

SUMMARY OF THE INVENTION

The invention provides a method for trapping signal sequence DNA from cDNA libraries comprising the steps of constructing a cDNA library in a signal trap vector for transformation into a yeast host cell and detecting secretion of a reporter polypeptide. The signal trap vector contains DNA encoding a reporter polypeptide which lacks a functional signal sequence. Secretion of the reporter polypeptide is indicative of the presence of functional signal sequence and may be detected by a variety of methods, including growth under certain nutrient conditions, enzyme activity or immune reactivity. A cDNA molecule encoding the full-length polypeptide containing the functional signal sequence is identified, cloned and expressed and the resulting polypeptide is isolated and purified.

The invention provides for a method for identifying a secreted mammalian protein comprising the steps of:
 a) constructing a mammalian cDNA library;
 b) inserting the cDNA library of step (a) into a signal trap vector to generate a signal trap library, wherein the vector comprises DNA encoding α-amylase lacking a functional signal sequence;
 c) amplifying the signal trap library of step (b);
 d) transforming the library of step (c) into a yeast host cell lacking a functional gene encoding α-amylase;
 e) selecting transformed yeast cells from step (d) for utilization of starch in growth medium;
 f) analyzing the DNA recovered from the transformed yeast cells of step (e) to determine whether a functional mammalian signal sequence is present; and
 g) screening a mammalian cDNA library to identify a full-length cDNA comprising the functional mammalian signal sequence of step (f).

The invention also relates to a cDNA molecule encoding a novel secreted mammalian protein and a novel secreted mammalian protein identified by employing steps (a) through (g) as set forth above.

The invention provides for a method for identifying a secreted mammalian protein comprising the steps of:

a) constructing a mammalian cDNA library;

b) inserting the cDNA library of step (a) into a signal trap vector to generate a signal trap library, wherein the vector comprises DNA encoding a reporter polypeptide, the reporter polypeptide being selected from the group consisting of melibiase and inulase, any of which lack a functional signal sequence;

c) amplifying the signal trap library of step (b);

d) transforming the library of step (c) into a yeast host cell lacking a functional gene encoding the selected reporter polypeptide of step (b);

e) selecting transformed yeast cells from step (d) for growth in selective medium requiring secretion of the reporter polypeptide;

f) analyzing the DNA recovered from the transformed yeast cells of step (e) to determine whether a functional mammalian signal sequence is present; and g) screening a mammalian cDNA library to identify a full-length cDNA comprising the functional mammalian signal sequence of step (f).

The invention also relates to a cDNA molecule encoding a novel secreted mammalian protein and a novel secreted mammalian protein identified by employing steps (a) through (g) as set forth above.

DETAILED DESCRIPTION OF THE INVENTION

Recombinant DNA techniques used herein are generally set forth in Sambrook et al., *Molecular Cloning: A Laboratory Manual*, Cold Spring Harbor Laboratory Press, Cold Spring Harbor, N.Y., (1989); by Ausubel et al., eds *Current Protocols in Molecular Biology*, Current Protocols Press, (1994); and by Berger and Kimmel, *Methods in Enzymology: Guide to Molecular Cloning Techniques*, Vol. 152, Academic Press, Inc., San Diego, Calif., (1987), the disclosures of which are hereby incorporated by reference.

Chemical synthesis of nucleic acid sequences can be accomplished using methods well known in the art, such as those set forth by Engels et al. *Angew. Chem. Intl. Ed.*, 28:716–734 (1989) and Wells et al. *Gene*, 34:315 (1985), the disclosures of which are hereby incorporated by reference. These methods include the phosphotriester, phosphoramidite and H-phosphonate methods of nucleic acid sequence synthesis. Large nucleic acid sequences, for example those larger than about 100 nucleotides in length, can be synthesized as several fragments and ligated together. A preferred method is polymer-supported synthesis using standard phosphoramidite chemistry.

As used herein, the terms "signal sequence", "leader sequence", and "secretion sequence" are used interchangeably and refer to N-terminal amino acid sequences capable of directing a polypeptide into the secretory pathway characteristic of eucaryotic cells. The term "reporter polypeptide" refers to polypeptides normally secreted by eucaryotic host cells which confer a property or activity when secreted which may be readily assayed (e.g, growth on selected media, enzymatic activity, reactivity with detecting reagents). Preferred examples of such reporter polypeptides are described below.

Methods for identifying signal sequence cDNA and novel secreted proteins (termed "signal sequence trapping") are provided by the invention. The methods employ signal trap vectors comprising DNA encoding nonsecreted reporter polypeptides. Introduction of DNA fragments encoding signal sequence DNA into the signal trap vectors result in the synthesis of a secreted reporter polypeptide which may be detected by various methods. After identification of signal sequences, full-length DNA clones encoding the secreted polypeptides may be isolated and expressed.

Secretion of a reporter polypeptide may be detected by utilization of a nutrient in a growth medium which requires secretion of the reporter polypeptide. In one embodiment, the reporter polypeptide is α-amylase which when secreted hydrolyzes starch. Secretion may also be detected by growth on selective medium requiring the presence of the secreted reporter polypeptide. In one embodiment, the reporter polypeptide is melibiase or inulase which are required for growth on melibiose and inulin carbon sources, respectively.

The invention also relates to a cDNA molecules encoding a novel secreted mammalian protein and a novel secreted mammalian protein identified by the methods of the invention.

cDNA libraries of the invention may be derived from any mammalian tissue or cell line. Messenger RNA (mRNA) isolation from a selected tissue or cell line and cDNA synthesis are carried out using published procedures. The population of cDNA molecules so obtained may be used without further modification to generate a signal trap library. Alternatively, cDNAs may be selected for the presence of 5' ends (PCT Publication No. WO96/40904) or may be selected for fragments of a desired size range prior to insertion into a signal trap vector. For example, DNA fragments of about 300 to 800 base pairs may be selected for insertion into yeast signal trap vectors. The fragments may be isolated by ion exchange chromatography, size exclusion chromatography, or gel electrophoresis. Optionally, the cDNA library may be fragmented to smaller sizes prior to fractionation.

Signal trap vectors of the invention will be suitable for replication and expression of secreted polypeptides in yeast. DNA sequences characteristic of such vectors include: an origin of replication, one or more selection or marker genes, a promoter sequence, one or more enhancer elements, a transcription termination sequence, reporter genes indicative of secretion, and the like. The vectors may also be used in bacterial host cells and may harbor at least an origin of replication and one or more selection or marker genes that are functional in bacterial host cells such as *E. coli*. These components may be obtained from natural sources or be synthesized by known procedures.

Origin of Replication

Signal trap vectors of the invention will have an origin of replication functional in yeast and may also have an origin of replication functional in bacteria. Yeast replication origins include cen, 2μ and autonomous replication sequence (ARS). Preferably, the origin is a 2μ origin. Replication origins functional in bacteria are well known (e.g., ColE1, F, or R1 based origins) and may give low or high copy numbers. A preferred origin of replication functional in bacteria is a ColE1-type such as that present on plasmid pBR322.

Selection Gene

A selection or marker gene encodes a polypeptide which allows for maintenance of the plasmid in a population of cells. Typical proteins include those that confer resistance to antibiotics or other toxins, or allow growth in the presence of specific nutrients. Examples of marker genes in yeast vectors include those involved in growth on specific sugar and amino acid substrates, such as trp, ura, leu, ade and his genes, which provide for maintenance of the plasmid in transformed yeast host cells lacking the corresponding functional genes on the host chromosome. Marker genes functional in bacterial hosts include those conferring antibiotic resistance such as ampicillin, chloramphenicol, kanamycin, and the like.

Promoter

Various promoters functional in yeast are known in the art and may include constitutive and inducible promoters. Examples of such promoters include adc, gal, pgk, pho, chelatin, and α-factor. Promoters in signal trap vectors will include additional 5' DNA sequence which provides for optimal activity, such as sequences necessary for promoter activation. Promoters suitable for use with prokaryotic hosts include the beta-lactamase and lactose promoter systems; alkaline phosphatase, a tryptophan (trp) promoter system; a bacterial luminescence (luxR) gene system and hybrid promoters such as the tac promoter. Other known bacterial promoters are also suitable.

Sequences of promoters mentioned herein have been published, thereby enabling one skilled in the art to ligate them to the desired DNA sequence(s) using linkers or adaptors as needed to supply any required restriction sites.

Enhancer Element

Enhancers are cis-acting elements of DNA, usually from about 10–300 bp in length, that act on the promoter to increase its transcription. Enhancers are relatively orientation and position independent. They have been found 5' and 3' to the transcription unit. Yeast enhancers are advantageously used with yeast promoters. Enhancers may act upon binding of an activator protein to increase transcription. Activator proteins include gal4, for activation of gal1 and gal10 promoters, and pho4 for activation of the pho5 promoter.

Reporter Genes

The reporter genes in signal trap vectors of the invention encode nonsecreted reporter polypeptides by virtue of lacking a functional signal sequence. In a preferred embodiment, DNA encoding a nonsecreted reporter polypeptide is lacking the signal sequence including the initiator methionine. The reporter polypeptide may also lack one or more additional amino acids from the mature amino terminus of the protein, provided that deletion of these amino acids does not alter the activity of the reporter polypeptide. Techniques for deleting DNA encoding signal peptides are available to one skilled in the art. Secretion of reporter polypeptides will occur upon inframe insertion of a functional mammalian signal sequence. The reporter polypeptides described below function in yeast, although other reporter polypeptides are suitable for bacterial or mammalian host cells.

Alpha (α)-amylase is a secreted enzyme that hydrolyzes starch into glucose. Laboratory strains of S. cerevisiae lack α-amylase and thus can not grow on starch. However, expression of active heterologous α-amylase in S. cerevisiae allows the host to hydrolyze starch to a certain degree. α-amylase from Lipomyces kononenkoe (Steyn et al. Curr. Genet. 28, 526–533 (1995); GenBank Accession No. U30376) can be expressed as an active enzyme in S. cerevisiae. Additionally, the enzyme contains a distinct secretory leader sequence that can be replaced with the cDNAs to perform secretion signal trap. The host expressing the secreted amylase can be phenotypically detected by loss of color (halo-formation) in the starch-containing medium surrounding the colony. This reporter could also be used in growth based assay when starch is provided as a sole carbon source.

Melibiase, the MEL1 gene product, also referred to as α-galactosidase, is a secreted protein that ferments melibiose into galactose and is readily absorbed by yeast. The presence of MEL1 in S. cerevisiae enables it to grow on melibiose as a sole carbon source. cDNA encoding melibiase (α-galactosidase) from S. cerivisiae has been described (Summner-Smith et al. Gene 36, 333–340 (1985); GenBank Accession No. M10604). The first nineteen amino acids of α-galactosidase constitute a typical eukaryotic secretion signal. Melibase lacking the secretion signal is no longer secreted and thus yeast cannot utilize melibiose as sole carbon source. In melibiase based signal trap, yeast recombinants that have effectively replaced the melibiase secretion signal can grow on medium containing melibiose as sole carbon source.

Inulinase, the INL1 gene product of Kluyveromyces marxianus, is a secreted protein which preferentially cleaves inulin, a storage polysachharide of plant origin. The precursor protein for inulinase has a typical signal peptide. The cDNA sequence has been described (Laloux et al. FEBS Letters 289, 64–68 (1991); GenBank Accession No. X57202). Similar to the melibase scheme, a growth selection signal trap can be designed using inulinase as reporter for secretion on a growth medium containing inulin as a sole carbon source.

Yeast acid phosphatase (Apase) is the Pho5 gene product that is secreted on the cell surface of yeast. The acid phosphatase has a distinct secretion signal peptide and thus can be replaced with mammalian cDNAs to trap secretion signals in yeast. Secretion can be readily detected by a color assay on plates. Apase substrates are unable to cross the plasma membrane, but the cell wall location of this enzyme allows it to be readily detected on plates overlaid with melted agar containing alpha-naphthyl phosphate and fast blue salt; positive colonies turn dark purple. Alternatively, on medium containing 5-bromo-4-chloro-3-indolyl phosphate (X—P), colonies expressing secreted phosphatase turn blue.

Transcription Termination

DNA sequences encoding transcription termination sites and polyadenylation of the 3' end of mRNA are also included in signal trap vectors. Transcription termination sites may be homologous or heterologous to the reporter gene being used. Examples of transcription terminators functional in yeast include adc, cyc, trp, α-factor, pgk, gal, ura, adh and flp. A transcription termination site may be positioned immediately 3' to the reporter polypeptide translational stop codon, or the site may be located further downstream from the translational stop.

Signal Sequence

As indicated above, the signal sequence is provided as part of cDNA library. cDNA fragments derived from the library are cloned into a signal trap vector to the 5' side of DNA encoding the mature, nonsecreted reporter polypeptide. Secretion is indicated by in-frame translation of a signal sequence and a reporter polypeptide.

The construction of signal trap vectors containing one or more of the above-listed components, with one of the reporter genes listed above, is accomplished by standard ligation techniques. Isolated plasmids or DNA fragments are cleaved, tailored and religated in the desired order to generate the vector required. To confirm that the correct sequence has been constructed, the ligation mixture may be used to transform *E. coli*, and successful transformants may be selected by known techniques as described above. Quantities of the vector from the transformants are then prepared, analyzed by restriction endonuclease digestion and/or sequenced to confirm the presence of the desired construct. Signal trap vectors are constructed such that DNA sequences which control expression of selection or marker genes, cDNA inserts and reporter genes are operably linked to said cDNA and genes. In addition, the cDNA libraries are generated in signal trap vectors such that potential signal sequences are inserted in frame to reporter polypeptide coding sequences.

In one embodiment, the signal trap vector is pYYA-41L. This plasmid is an *E. coli*-yeast shuttle vector that contains a Bla1 gene (for ampicillin resistance) and ColE1-ORI (replication origin) for maintenance and propagation in *E. coli* and a $2\mu$ origin of replication and TRP1 gene for propagation in yeast. It also contains in order 5' to 3':an ADH promoter, a polylinker to facilitate directional cloning of cDNAs, a leaderless α-amylase gene encoding amino acids 29–624 of α-amylase (designated Δ28LKA1), and an ADH terminator sequence. The unique XhoI and Not I in the polylinker is used for directional cloning of random primed cDNAs to create fusions with Δ28LKA1. It will be recognized that other vectors may be constructed having alternative replication origins, selection genes and promoters, for example, when would be equally useful in signal trapping.

The vector pYYA-41L has been deposited with the American Type Culture Collection, Rockville, Md. 20852 on Feb. 13, 1998 on under accession no. 986559. Deposit of this material does not create any presumption that the material is necessary to satisfy 35 U.S.C. 112 or that deposit in accordance with these regulations is or was required.

Host cells of the invention for detecting secreted proteins may be any host which has a secretory pathway characteristic of mammalian cells. Preferred host cells include yeast and fungi, and particularly the genus Saccharomyces. Preferred embodiments include *Saccharomyces cerivisiae*. Yeast has an advantage of short life cycle, high transformation efficiency and choice of single and high copy plasmid systems. The yeast secretory machinery is similar to that of mammalian cells.

Host cells for amplifying cDNA libraries are bacterial host cells, and preferably *E.coli*. Said host cells include but are not limited to eubacteria such as Gram-negative or Gram-positive organisms (e.g., *E. coli* (HB101, DH5α, DH10B and MC1061); Bacilli such as *B. subtilis*; Pseudomonas species, such as *P. aeruginosa*; Streptomyces spp.; *Salmonella typhimurium*; or *Serratia marcescans*. As a specific embodiment, a desired protein may be expressed in *E. coli*.

Techniques for transforming a yeast host cell with plasmid DNA are known in the art. A host cell may be transformed with a desired nucleic acid under appropriate conditions permitting expression of the nucleic acid. The selection of suitable yeast host cells and methods for transformation, culture, amplification, screening and product production and purification are carried out using published procedures. (Becker and Guarente: *Guide to Yeast Genetics and Molecular Biology*, Academic Press, Inc., San Diego, Calif. (1991)).

Transformed or transfected host cells are cultured in nutrient medium in a manner that allows stable maintenance of the resident recombinant plasmid, amplification of plasmid copy number, and expression and secretion of recombinant polypeptides encoded by said plasmids. In general, yeast host cells are cultured on rich (YPD) medium or SD CAA nutrient selection medium. In general, bacterial host cells are cultured on rich (LB) or minimal salts medium optionally supplemented with antibiotics for plasmid selection.

Detection of signal sequence DNA may be accomplished by a variety of methods depending upon reporter polypeptide and the host cell used. Although the reporter protein could either be of yeast, mammalian, or bacterial origin, it is preferably of yeast origin. The assays described below are carried out in yeast strains which naturally lack the reporter gene or in which the reporter gene has been inactivated by mutation (e.g., deletion, insertion, or one or more base changes which alter the amino acid sequence).

Growth Selection

The secreted reporter polypeptides in this category are essential for growth of yeast host cells on a defined medium. Secreted enzymes in the sugar uptake pathway of yeast, such as melibiase for growth on melibiose or inulase for growth on inulin, can be used as reporters for growth on appropriate sugar source. The yeast lacking a functional gene for the specific carbon source utilizing enzyme can be used for the assay. Transformed yeast containing a signal trap vector into which cDNA library fragments have been inserted are selected for growth on the appropriate sugar source. Such a selection pressure should allow growth of only yeast containing mammalian secretion signal fused in frame with the reporter gene.

Selective growth assays other than those based on carbon sources may also be utilized; for instance, selection based on utilization of organic phosphate.

Enzyme Activity

An enzymatic reporter polypeptide, upon successful secretion, hydrolyzes a substrate to effect a change in the color of a yeast colony or its immediately adjacent area. Analogous to the growth-based assays, the secretion signal of the reporter is removed and replaced with the cDNA library. The recombinants containing reporter gene fused to the mammalian secretory signals that allow successful secretion are detected by adding appropriate substrate for the reporter enzyme into the growth media which upon cleavage gives a discernible phenotype. In this scheme, no selection pressure is applied for secretion (as in the growth assay) and all recombinants grow, whether or not they secrete the reporter enzyme. Positive colonies are distinguished visually. One example of a reporter polypeptide of this type is α-amylase.

A similar assay can be setup with secreted alkaline phosphatases from other species. For instance, bacterial alkaline phosphatase or human placental alkaline phosphatase, may be used as the reporter enzyme in yeast. Phosphatases are also amenable to FACS sorting based selection using a fluorescent phosphatase substrate to label the positive cells. Thus recombinants that allow secretion of phosphatase can be doubly selected by sorting followed by a color assay on plates.

Putative signal sequences obtained by one of the above screening methods are further characterized by isolation and sequencing of the cloned cDNA insert using conventional techniques and analysis of the sequences so obtained. Typically, the sequence of the cDNA insert directing secretion of the reporter polypeptide will be compared to known signal sequences present in publicly available databases such as SwissProt or GenBank (translated). Sequence alignment programs such as those available in the GCG Sequence Analysis programs (University of Wisconsin) are useful for identifying regions of homology between the cDNA inserts that scored positive on secretion screens and known signal sequences.

As further confirmation that a novel sequence is indeed a signal sequence, part or all of the sequence of the cDNA insert directing secretion of the reporter polypeptide may be used as probe to identify the DNA sequence encoding the full-length polypeptide. The probe may be used in hybridization or PCR reactions to identify the coding sequence present in a cDNA, genomic DNA, or synthetic DNA library. Expression of the DNA sequence encoding the full-length polypeptide in a mammalian host cell and secretion of the resulting polypeptide would confirm that the novel sequence identified in the secretion screen is a signal sequence.

Conditions for screening DNA libraries by hybridization using cDNA fragments of about 300 to 800 base pairs as probes are set forth in Sambrook et al. supra, pp. 387–389. Hybridization and washing are typically carried out under conditions that favor annealing of highly homologous regions of DNA taking into account factors such as the size of the DNA fragments used as probes and the complexity of the. library being screened. Preferably, the washing is carried out under high stringency conditions. Examples of stringent washing solutions, which are usually low in ionic strength and are used at relatively high temperatures, are as follows: one such stringent wash is 0.015 M NaCl, 0.005 M Na Citrate and 0.1% SDS at 55–65° C.; another such stringent wash is 1 mm $na_2edta$, 40 mm $nahpo_4$, ph 7.2, and 1% SDS at about 40–50° C.; and one other stringent wash is 0.2×SSC and 0.1% SDS at about 50–65° C.

There are also exemplary protocols for stringent washing conditions where oligonucleotide probes are used for hybridization. For example, a first protocol uses 6×SSC with 0.05 percent sodium pyrophosphate at a temperature of between about 35° C. and 63° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where the background non-specific binding appears high. A second protocol uses tetramethylammonium chloride (TMAC) for washing. One such stringent washing solution is 3 M TMAC, 50 mM Tris-HCl, pH 8.0 and 0.2% SDS.

A cDNA library may also be screened for genes encoding full-length polypeptides by PCR using primers based upon the sequences obtained by signal trap cloning. Procedures for amplifying sequences by PCR are described in Ausbel et al., supra.

Novel full-length secreted mammalian polypeptides are assayed for biological activity by various methods. In one method, the polypeptides are expressed by recombinant methods known in the art, such as transient expression in transfected COS cells or, if greater quantities of protein are desired, expression in stable transfectants such as CHO cells. Conditioned growth medium may be assayed directly for biological activity or the polypeptide may be partially or substantially purified using procedures known in the art prior to assay for activity. In this approach, a particular assay may be employed based upon a postulated activity for the secreted polypeptide. Biological activity may be surmised based upon sequence homology to other proteins of known function, patterns of expression in tissues of developing and mature animals (especially when expression is limited to one or a few tissues), a combination of sequence homology and tissue expression, or some other criteria. In vitro assays are typically used to initially identify an activity of a novel protein and may be followed up by appropriate in vivo assays.

Alternatively, novel secreted proteins may be introduced into transgenic animals in order to directly determine in vivo activity in a whole animal. In one embodiment, a novel secreted mouse or rat protein is expressed as a transgene in a mouse or a rat. Suitable transgenic expression vectors, transfection procedures and expression of foreign transgenes have been previously described (see PCT Publication No. 97/23614, the relevant portions of which are hereby incorporated by reference). The effects of systemic expression of a novel secreted protein may be evaluated by pathology analysis of transgene expressors, including histologic, histochemical and immunohistochemical analysis.

The following examples are offered to more fully illustrate the invention, but are not to be construed as limiting the scope thereof.

EXAMPLE 1

Vectors for α-amylase Based Yeast Signal Trap

Plasmid pAJC2 containing *Lipomiyces kononenkoe* cDNA encoding α-amylase has been previously described (Steyn et al. Curr. Genetics 28, 526–523 (1995)). The cDNA(LKA1) sequence of the *Lipomiyces kononenkoe* α-amylase gene is available as GenBank Accession No. U30376. The full length and deletion mutants of LKA1 gene were obtained by polymerase chain reaction (PCR) amplification and cloned into a modified yeast expression vector pGBT9 (Clonetech). In this vector, sequences between the alcohol dehydrogenase (ADH) promoter and ADH terminator were removed and replaced by a polylinker which has restriction sites in the following order: HindIII-XhoI-SalI-EcoRI-SmaI-BamHI-SpeI-SphI-NotI-XhoI-SstI. LKA1 cDNA encoding the entire open reading frame (amino acids 1–624 wherein the amino terminal methionine residue is residue 1) of α-amylase was cloned using a sense primer (1509-81):

AGTCCTCGAGCAACAATGTTGCTGATCAACT (SEQ ID NO:1)

and an anti-sense primer (1509-83):

AGTCGAGCTCTCTACATGGAGATTC (SEQ ID NO:2)

The 5' oligonucleotide contained a XhoI site and the 3' oligonucleotide contained an SstI restriction site. The PCR product was digested with XhoI and NotI and cloned into the expression vector at corresponding sites. This vector was designated pYYA-42L.

Truncated LKA1 cDNA corresponding to amino acids 29–624 and lacking the secretion signal sequence was cloned using 5' primer (1509-82):

AGTCGCGGCCGCGGATTGCACTACAGTTACGGT (SEQ ID NO:3)

Truncated α-amylase encoding amino acids 82–624 was cloned using 5' primer (1598-37):

AGTCGCGGCCGCAGCGATACATCTGTGACATAC (SEQ ID NO:4)

In both cases the anti-sense primer was 1509-83. The 5' oligonucleotides included a NotI restriction site. PCR amplified products were digested with NotI and SstI restriction enzymes and cloned into the expression vector. These two vectors, respectively named pYYA-41L and pYYA-2, were used for signal trapping from the mammalian cDNAs.

EXAMPLE 2

Secretion of α-amylase by heterologous signal peptides

DNA fragments encoding the amino portions of erythropoietin (EPO), actin 2 (ACT2), monocyte chemotactic and activating factor (MCAF), leukemia inhibiting factor (LIF), interleukin-10 (IL-10), and interleukin-6 (IL-6), including the signal peptides, were synthesized by PCR using 5' and 3' primers. A Sal I site was inserted in front of the start codon in each of the 5' primers, and a Not I site was inserted in the 3' primer. Amino terminal portions of EPO corresponded to amino acid residues 1-27, 1-60, 1-93, 1-127, 1-160, and 1-193 where the amino terminal methionine is designated residue 1 (see U.S. Pat. No. 4,703,008). EPO fragments were individually amplified using a common 5' primer (1464-32):

The PCR fragments were cleaned, digested with SalI and NotI and ligated to vector pYYA-41L which had been digested with XhoI and NotI. The ligation of these fragments created in-frame fusions of truncated EPO fragments containing signal peptide with the leaderless amylase. The ligation mixtures were transformed into *E. coli* DH10B cells by electroporation. Plasmid DNAs were prepared and analyzed for correct insert sizes by restriction enzyme digestion and agarose gel electrophoresis as described (Sambrook et al. supra). The identity of the inserted DNA was confirmed by sequencing.

The utility of these signal peptides for secretion of amylase was determined by testing the ability of these fusion proteins to form halos on the yeast selection medium plates

```
         AGCTGTCGACATGGGGGTGCACGAATGTCCT       (SEQ ID NO:5)
along with, respectively, these 3' anti-sense primers:

1464-33  AGCTGCGGCCGCCAGGACTGGGAGGCCCCAGA      (SEQ ID NO:6)

1464-34: AGCTGCGGCCGCGTGTTCAGCACAGCCCGTCG      (SEQ ID NO:7)

1464-35: AGCTGCGGCCGCGCCCTGCCAGACTTCTACGG      (SEQ ID NO:8)

1464-36: AGCTGCGGCCGCGACGGCTTTATCCACATGCAG     (SEQ ID NO:9)

1464-37: AGCTGCGGCCGCTGTTCGGAGTGGAGCAGCTG      (SEQ ID NO:10)

1464-38: AGCTGCGGCCGCTCTGTCCCCTGTCCTGCAGG      (SEQ ID NO:11)
```

Similarly, cDNA sequences corresponding to the first 92 amino acids of human ACT2 (GenBank accession no. J04130), 99 amino acids of human MCAF (GenBank accession no. M24545), approximately 100 amino acids of LIF (Gen Bank Accession No. X13967), 100 amino acids of human IL10 (GenBank accession no. M57627) and 106 amino acids of human IL6 (GenBank accession no. M14584) were amplified by PCR using the following sense and antisense primer sets, respectively: 1539-72 and 1539-73; 1539-74 and 1539-75; 1539-78 and 1539-79; 1539-80 and 1539-81; and 1539-70 and 1539-71. The DNA sequences of these primers are as follows:

containing starch azure. The plasmid DNA was transformed into yeast strain YPH499 (ATCC accession no. 90834) by the LiOAC procedure. The transformed cells were plated onto minimal selection medium supplemental with 0.75% starch azure. Plates were incubated for 4 to 5 days at 30° C. and then examined visually for halo formation around the yeast colonies. The results of the amylase fusions containing heterologous amino terminal sequences of variable sizes from various known secreted proteins are summarized in Table 1.

```
1539-72: AGTCGTCGACATGAAGCTCTGCGTGACTG         (SEQ ID NO:12)

1539-73: AGTCGCGGCCGCGTTCAGTTCCAGGTCATAC       (SEQ ID NO:13)

1539-74: AGTCGTCGACATGAAAGTCTCTGCCGCCC         (SEQ ID NO:14)

1539-75: AGTCGCGGCCGCAGTCTTCGGAGTTTGGGTTTG     (SEQ ID NO:15)

1539-78: AGTCGTCGACATGAAGGTCTTGGCGGCA          (SEQ ID NO:16)

1539-79: AGTCGCGGCCGCACATAGCTTGTCCAGGTTG       (SEQ ID NO:17)

1539-80: AGTCGTCGACATGCACAGCTCAGCACTG          (SEQ ID NO:18)

1539-81: AGTCGCGCCGCGTTCTCAGCTTGGGCAT          (SEQ ID NO:19)

1539-70: AGTCGTCGACATGAACTCCTTCTCCACAAG        (SEQ ID NO:20)

1539-71: AGTCGCGGCCGCGAATCCAGATTGGAAGCATC      (SEQ ID NO:21)
```

TABLE 1

| Signal peptide | Amylase secretion* |
|---|---|
| α amylase w/o signal seguence | — |
| Full length α amylase | ++++ |
| EPO- [1-193] | ++ |
| EPO- [1-93] | +++ |
| EPO- [1-27] | ++++ |
| ACT2 [1-92] | +++ |
| IL6 [1-106] | ++ |
| IL10 [1-100] | ++ |
| MCAF [1-99] | +++ |

— indicates no halo formation
+ to ++++ indicate halo formation and halo sizes in ascending order.

The results showed that the vector containing leaderless amylase was unable to form halo, whereas plasmid carrying full-length amylase or various fusions with the leaderless amylase resulted in halo formation surrounding the yeast colonies. However, noticeable differences were observed in halo sizes as summarized in the table. Thus, signal peptides from hetrologous proteins could confer secretion to a truncated leaderless amylase. Additionally, large fusions could be tolerated without compromising the secretion and activity of amylase. Thus, this vector could be utilized for trapping signal peptide-encoding sequences from directionally cloned random cDNA libraries. Similar results were obtained when EPO and ACT2 signal sequence fragments were tested in vector pYYA-2.

EXAMPLE 3

Identification of Signal Sequence DNA by α-amylase Signal Trapping

Construction of cDNA Libraries

One gram of each appropriate frozen mouse tissue sample was homogenized in 20 ml TRIzol Reagent (Gibco BRL, Bethesda, Md., Catalog no. 15596-018). Samples were incubated 5 minutes at room temperature, and 4 ml chloroform was added. Samples were centrifuged at 9000×g, and the aqueous phase was transferred into a fresh tube. 10 ml of isopropyl alcohol was mixed in and the samples were incubated for 10 minutes at room temperature. Total RNA was precipitated by centrifugation at 12,000×g for 20 minutes. RNA pellet was then washed two times with 75% ethanol and air dried. Poly A+ RNA was isolated from the total RNA using the mRNA Separator Kit following the manufacturer's protocol (Clontech Laboratories, Palo Alto, Calif., Catalog no. K1040-2). The cDNA library was made using the SuperScript™ Plasmid System for cDNA Synthesis (Gibco/BRL, Catalog no. 18248-013) with minor modifications. Briefly, to make the random-primed cDNA libraries, first strand synthesis was done using the following oligonucleotide:

1360-38: GGAAGGAAAAAAGCGGCCGCAA-CANNNNNNNNN (SEQ ID NO:22)

that contained nine random nucleotides following a Not I restriction site. Five μg of poly A RNA and 500 ng of the primer was used in the first strand synthesis.

Second strand synthesis and Sal adapter ligation was done according to the manufacturer's protocol. After Not I digestion, cDNA was purified using the QIAquick PCR Purification Kit (QIAGEN Inc, Chatsworth, Calif., Catalog no. 28104). The cDNA was size fractionated on a 1% L.M.P. Agarose gel (Gibco BRL, Catalog no. 15517-022). The gel region containing cDNA fragments in the size range of between 300–800 base pairs was excised and the DNA extracted with phenol as follows: 50 μl of 5M NaCl was added and incubated at 70° C. for 5 minutes. An equal volume of phenol was then mixed in by vortexing. The aqueous phase was obtained by centrifuging at 14,000 rpm for 10 minutes. After phenol-chloroform extraction, cDNA was precipitated following standard protocol. The cDNAs were then ligated into the Xho I and Not I digested pYYA-41L plasmid. The ligation was carried out in 20 μl total volume containing 100 ng of vector DNA, 20 ng of cDNA, 1×ligase buffer, and 1 μl of T4 ligase at 16° C. for 20 hours. The ligated DNAs were precipitated, and introduced into ElectroMAX electrocompetent E. coli strain DH10B (Gibco BRL, Catalog no. 18290-015) by electroporation at 1.8 kV, 200 ohms, and 25 mFd in 0.1-cm cuvettes (Invitrogen, Inc., Carlsbad, Calif., Catalog no. 1724-51). The transformed bacteria cells were grown in 5 ml SOC at 37° C. for 1 hour, and then frozen at −80° C. with 10% glycerol. Transformation mix was first titrated for colony forming units. Approximately 50,000 bacteria were plated on 150 mm LB agar plate with 100 μg/ml ampicillin. Plasmid DNA of the cDNA library was prepared in pools of 250,000 cfu each. The plates were incubated at 37° C. overnight. Bacterial colonies from five 150 mm plates were scraped into 50 ml LB. The cells were pelleted by spinning in 50 ml conical tubes at 4000 rpm for 10 minutes. The plasmid DNA was prepared by using QIAGEN maxi prep kit.

Yeast Transformation

Yeast strain YPH499 (Matα ura3-52 lys2-801 ade2-101 trp1-D63 his3-D200, leu2-D1; GenBank Accession No. 98034) was used as transformation host. Yeast transformation with individual plasmid DNA or cDNA libraries was done using LiOAc procedure. For large scale cDNA library transformations, yeast competent cells were made as follows: a single colony of yeast was inoculated into 50 ml YPD medium (1% yeast extract, 2% DIFCO peptone, 2% glucose) and grown overnight, with shaking at 30° C. This overnight culture was diluted to $OD_{600}$=0.2–0.3 in 500 ml YPD and incubated with shaking at 30° C. for an additional 4 to 5 hours, for approximately one doubling. Cells were harvested by centifugation at 5000 rpm for 5 minutes, and pellets were washed once with 250 ml sterile water and resuspended in 6.4 ml 1×LiOAc/TE solution (0.1 M LiOAc, 10 mM Tris-HCl pH7.5, 1 mM EDTA).

To obtain about 250,000 yeast transformants, 40 μg of library cDNA in pYYA-41L yeast vector was transformed into yeast competent cells. The transformation mixture contained 40 μg cDNA library, 4 mg denatured salmon sperm DNA, 6.4 ml competent cells, and 40.8 ml PEG/LiOAc (40% PEG-4000, 0.1 M LiOAc, 10 mM Tris-HCl pH 7.5, 1 mM EDTA). The mixture was incubated at 30° C. with shaking. 5.2 ml dimethylsulfoxide (DMSO) was then added, and the mix was heat shocked at 42° C. for 15 minutes with occasional swirling. Cells were pelleted by centrifugation at 2500 rpm for 5 minutes. Pellet was washed once with 100 ml sterile water, resuspended in 10 ml sterile water and plated onto 50 SD CAA trp—SA plates (0.67% yeast nitrogen base, 2% glucose, 0.1% CAA, 1×trp dropout solution, 1.5% agar, 0.7% potato starch azure) to obtain about 5000 colonies on each 150 mm plate. Even spreading of yeast transformation mix was achieved by adding 4-mm glass beads (Fisher Scientific, Pittsburgh, Pa., Catalog no. 11-312B) and rocking the plates back and forth. The plates were incubated for 4–5 days at 30° C. until α-amylase-secreting colonies started forming halos. Halo forming clones were obtained at a frequency between 1/300 to 1/600.

Analysis of DNA from α-amylase Secreting Colonies

Halo forming colonies were picked and streaked onto fresh selective medium plates containing starch azure. Single isolated colonies were then picked into 100 μl of sterile distilled water in 96-well titer plates. 15 ml of this yeast suspension was used to PCR amplify the cDNA insert using vector specific primers. The 5' vector specific-primer corresponding to the ADH promoter was:

1655-89: CGTCATTGTTCTCGTTCC (SEQ ID NO:23)

The 3' vector specific anti-sense primer corresponding to α-amylase sequence was: 1510-02: ACTAGCTCCAGT-GATCTC (SEQ ID NO:24)

PCR was performed using the following conditions: 94° C. for 10 min. followed by 30 cycles of the following: 94° C. for 30 seconds, 55° C. for 30 seconds, 72° C. for 1.5 minutes; plus a 10-minute final extension at 72° C. The PCR amplified products were cleaned and further analyzed by DNA sequencing. The following vector-specific nested primers:

1539-19: GCTATACCAAGCATACAATC (SEQ ID NO:25) and 1529-05: CTAGCTGGACATGGTTCG (SEQ ID NO:26)

were used for sequencing the cDNA fragments.

DNA sequences were analyzed by computer algorithms that are designed to predict the occurrence of signal sequences with a high degree of certainty. Based on these predictions the frequency of cDNAs encoding secreted proteins ranged between 20–40%. In addition to enrichment of secreted proteins, the α-amylase signal trap procedure enriched for proteins with transmembrane domains, such as transporters, internal membrane proteins, G-coupled and tyrosine kinase receptors. It was estimated that α-amylase signal trap can enrich for clones having signal sequences by several fold.

Full-length DNA clones are isolated from cDNA which directed secretion of a leaderless α-amylase gene and had a predicted secretion signal and/or transmembrane domain. Cloning of the full-length genes corresponding to the cDNA clones obtained by signal trapping may be carried out using methods which are well known by those skilled in the art. For example, the nucleic acid sequence is used as a probe to obtain a full length clone from an oligo dT primed cDNA library, or cDNA sequence specific primers are designed for performing 3' RACE by using commercially available reagents.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. A method for identifying a novel secreted mammalian protein comprising the steps of:

a) constructing a mammalian cDNA library;
   b) inserting the cDNA library of step (a) into a signal trap vector to generate a signal trap library, wherein the vector comprises DNA encoding α-amylase lacking a functional signal sequence;
   c) amplifying the signal trap library of step (b);
   d) transforming the library of step (c) into a yeast host cell lacking a functional gene encoding α-amylase;
   e) selecting transformed yeast cells from step (d) for utilization of starch in growth medium;
   f) analyzing the DNA recovered from the transformed yeast cells of step (e) to determine whether a functional mammalian signal sequence is present; and
   g) screening a mammalian cDNA library to identify a full-length cDNA comprising the functional mammalian signal sequence of step (f).

2. A method for identifying a novel secreted mammalian protein comprising the steps of:

a) constructing a mammalian cDNA library;
   b) inserting the cDNA library of step (a) into a signal trap vector to generate a signal trap library, wherein the vector comprises DNA encoding a reporter polypeptide, the reporter polypeptide being selected from the group consisting of melibiase and inulase, any of which lack a functional signal sequence;
   c) amplifying the signal trap library of step (b);
   d) transforming the library of step (c) into a yeast host cell lacking a functional gene encoding the selected reporter polypeptide of step (b);
   e) selecting transformed yeast cells from step (d) for growth in selective medium requiring secretion of the reporter polypeptide;
   f) analyzing the DNA recovered from the transformed yeast cells of step (e) to determine whether a functional mammalian signal sequence is present; and
   g) screening a mammalian cDNA library to identify a full-length cDNA comprising the functional mammalian signal sequence of step (f).

* * * * *

UNITED STATES PATENT AND TRADEMARK OFFICE
CERTIFICATE OF CORRECTION

PATENT NO. : 6,103,472
DATED : August 15, 2000
INVENTOR(S) : Sushil K. Thukral

It is certified that error appears in the above-identified patent and that said Letters Patent is hereby corrected as shown below:

Column 11, line 24: Change "AGCTGCGGCCGCCAGGACTGGGAGGCCCCAGA" to -- AGCTGCGGCCGCCAGGACTGGGAGGCCCAGA --

Signed and Sealed this

Twenty-fourth Day of April, 2001

Attest:

Attesting Officer

NICHOLAS P. GODICI

Acting Director of the United States Patent and Trademark Office